US00PP11973P2

(12) United States Plant Patent
Persoff

(10) Patent No.: US PP11,973 P2
(45) Date of Patent: Jul. 3, 2001

(54) MIMULUS PLANT NAMED 'JELLY BEAN YELLOW'

(76) Inventor: Richard Persoff, P.O. Box 2918, Alameda, CA (US) 94501

( * ) Notice: Subject to any disclaimer, the term of this patent is extended or adjusted under 35 U.S.C. 154(b) by 0 days.

(21) Appl. No.: 09/606,126

(22) Filed: Jun. 28, 2000

(51) Int. Cl.[7] ..... A01H 5/00

(52) U.S. Cl. ..... Plt./263
(58) Field of Search ..... Plt./263

*Primary Examiner*—Bruce R Campell
(74) *Attorney, Agent, or Firm*—C. A. Whealy

(57) ABSTRACT

A distinct cultivar of Mimulus plant named 'Jelly Bean Yellow', characterized by its upright, somewhat spreading, mounding and compact plant habit; freely branching habit; moderate to high vigor; and numerous golden yellow flowers.

2 Drawing Sheets

BACKGROUND OF THE INVENTION

The present invention relates to a new and distinct cultivar of Mimulus plant, botanically known as *Mimulus aurantiacus*, and hereinafter referred to by the cultivar name Jelly Bean Yellow.

The new Mimulus is a product of a planned breeding program conducted by the Inventor in Alameda, Calif. The new Mimulus originated from a cross made by the Inventor of two unidentified selections of *Mimulus aurantiacus*. The new Mimulus was selected in 1998 on the basis of its compact and freely flowering habit.

Asexual reproduction of the new cultivar by terminal cuttings taken at Alameda, Calif., has shown that the unique features of this new Mimulus are stable and reproduced true to type in successive generations.

SUMMARY OF THE INVENTION

Plants of the cultivar Jelly Bean Yellow have not been observed under all possible environmental conditions. The phenotype may vary somewhat with variations in environment such as temperature, light intensity, daylength, and nutritional status without, however, any variance in genotype.

The following traits have been repeatedly observed and are determined to be the unique characteristics of 'Jelly Bean Yellow'. These characteristics in combination distinguish 'Jelly Bean Yellow' as a new and distinct cultivar:

1. Upright, somewhat spreading, mounding and compact plant habit.
2. Freely branching habit.
3. Moderate to high vigor.
4. Numerous golden yellow flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Mimulus.

The photograph on the first sheet comprises a side perspective view of a typical flowering plant of 'Jelly Bean Yellow' grown in a 15-cm container.

The photograph at the top of the second sheet is a close-up view of typical flowering stems of 'Jelly Bean Yellow'.

The photograph at the bottom of the second sheet is a close-up view of typical flowers and the upper and lower surfaces of typical leaves of 'Jelly Bean Yellow'.

DETAILED BOTANICAL DESCRIPTION

In the following description, color references are made to The Royal Horticultural Society Colour Chart except where general terms of ordinary dictionary significance are used. Plants grown in 15-cm containers were used for the following description with one plant per container. Plants were grown in polyethylene-covered greenhouses and under conditions which closely approximate commercial production conditions during the spring in Encinitas, Calif. Day temperatures averaged about 18° C., night temperatures averaged about 10° C., and light levels were about 5,000 to 6,000 foot-candles.

Botanical classification: *Mimulus aurantiacus* cultivar Jelly Bean Yellow.

Parentage:

*Female parent.*—Unidentified selection of *Mimulus aurantiacus*, (unpatented).

*Male parent.*—Unidentified selection of *Mimulus aurantiacus*, (unpatented).

Propagation:

*Type cutting.*—Terminal vegetative cuttings.

*Time to initiate roots, summer.*—About 14 days at 20° C.

*Root description.*—Numerous, fine.

Plant description:

*Form.*—Mostly upright, somewhat spreading, mounding and compact plant habit.

*Usage.*—Appropriate for 15-cm containers.

*Crop time.*—About 18 weeks are required to produce finished flowering plants in 15-cm containers.

*Plant height.*—About 30 cm.

*Area of spread.*—About 37 cm.

*Vigor.*—Moderate to high vigor.

*Branching habit.*—Freely branching with about four lateral branches per plant; removal of terminal apices (pinching) enhances branching.

*Lateral branches.*—Length: About 19.5 cm. Diameter: About 3 mm. Internode length: About 3.6 cm. Texture: Viscid; glabrous. Color: 144C.

*Foliage description.*—Leaves simple, generally symmetrical and long persisting; opposite. Quantity per lateral branch: Typically about 20. Length: About 5.75 cm. Width: About 1.6 cm. Aspect: Slightly reflexed. Shape: Elliptic. Apex: Rounded acute. Base: Attenuate. Margin: Entire with minute ciliation. Texture: Viscid; glabrous; leathery. Color: Young Foliage, upper surface: 146B; somewhat glossy. Young foliage, lower surface: 146C. Mature foliage, upper surface: 146A; somewhat glossy; venation, 146A. Mature foliage, lower surface: 146C; venation, 146C. Petiole: Length: About 4 mm. Diameter: About 4 mm. Color: 144C.

Flower description:

*Flower type and habit.*—Medium to large-sized flowers; flowers face mostly outward; single, axillary; salverform, zygomorphic. Flowers persistent.

*Natural flowering season.*—Flowering typically from early spring until fall; about 10 weeks from planting to flowering.

*Quantity.*—Freely and continuous flowering; typically about 70 flower buds and opened flowers per plant.

*Fragrance.*—Not detected.

*Flower longevity on the plant.*—About 3 days.

*Flower buds (showing color).*—Length: About 2.65 cm. Diameter: About 7 mm. Shape: Elongate. Color: 15B.

*Corolla.*—Arrangement/appearance: Five-parted, fused into a tube; lobes, flared. Flower diameter: Vertical axis, about 4 cm; horizontal axis, about 3.5 cm. Flower depth (length): About 5.5 cm. Flower tube length: About 5.2 cm. Petal length: About 5.65 cm. Petal width: About 1.5 cm. Petal shape: Fan-shaped; lobes irregularly sinuate and ruffled; upper two lobes, reflexed. Texture: Smooth, satiny. Color: Petal, upper surface, when opening: 17A. Petal, lower surface, when opening: 23B to 23C. Petal, upper surface, opened flower: 15B, fading to 15C with development. Petal, lower surface, opened flower: 15C to 15D. Flower throat (inside): White, 155A, with two nectar guides, 23A, at base of lower lobe. Flower tube (outside): 15C to 15D.

*Sepals.*—Quantity: Five, fused. Shape: Elliptic; folded at midveins; calyx, zygomorphic tube. Calyx length: About 2 to 3 cm. Calyx diameter: About 8 mm. Apex: Acute. Margin: Entire. Texture: Slightly viscid; coarse with white hairs. Color: Upper surface: 144B. Lower surface: 144A.

*Peduncle.*—Strength: Good. Angle: Somewhat upright to nearly horizontal, about 55 to 90° to the stem. Length: About 6 mm. Color: 144B.

*Reproductive organs.*—Stamens: Quantity: Four total, two shorter than the other two. Anther shape: Ovoid. Anther size: About 2 by 1 mm. Anther color: 1C. Pollen amount: Scarce. Pollen color: 1D. Pistils: Pistil quantity per flower: One. Pistil length: About 3.7 cm. Stigma shape: Flattened, bi-lobed. Stigma color: 155D. Style length: About 3.2 cm. Style color: 155A to 155B. Ovary color: 144B.

*Seed.*—Seed production has not been observed.

Disease resistance: Plants of the new Mimulus have not been noted to be resistant to pathogens common to Mimulus.

It is claimed:

1. A new and distinct cultivar of Mimulus plant named 'Jelly Bean Yellow', as illustrated and described.

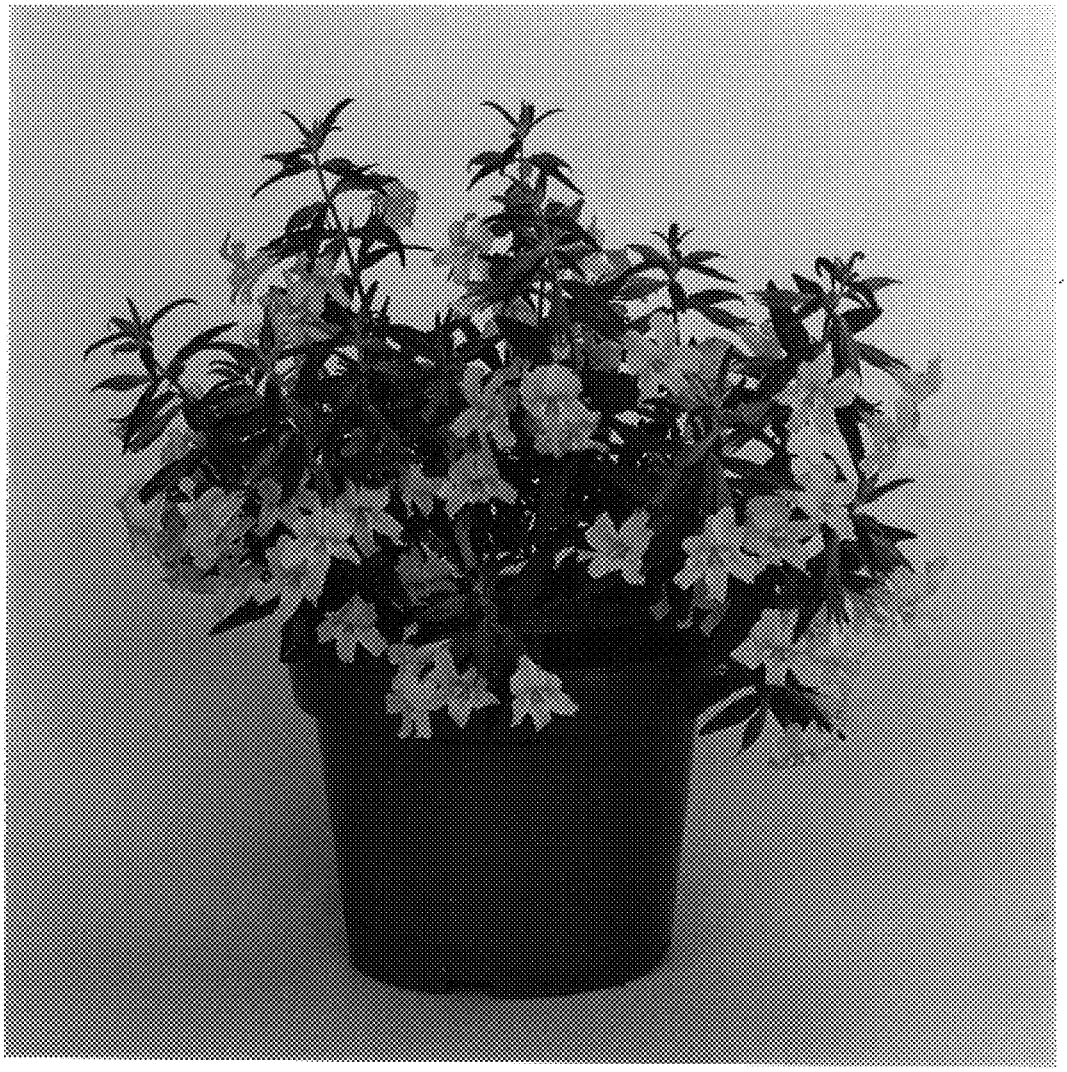

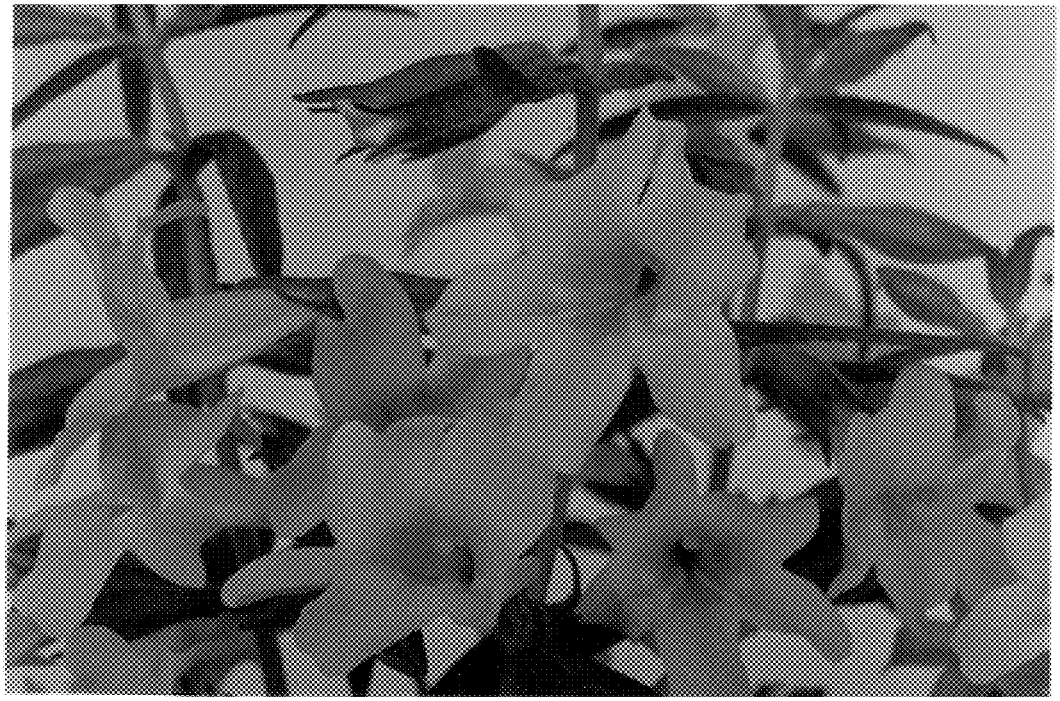
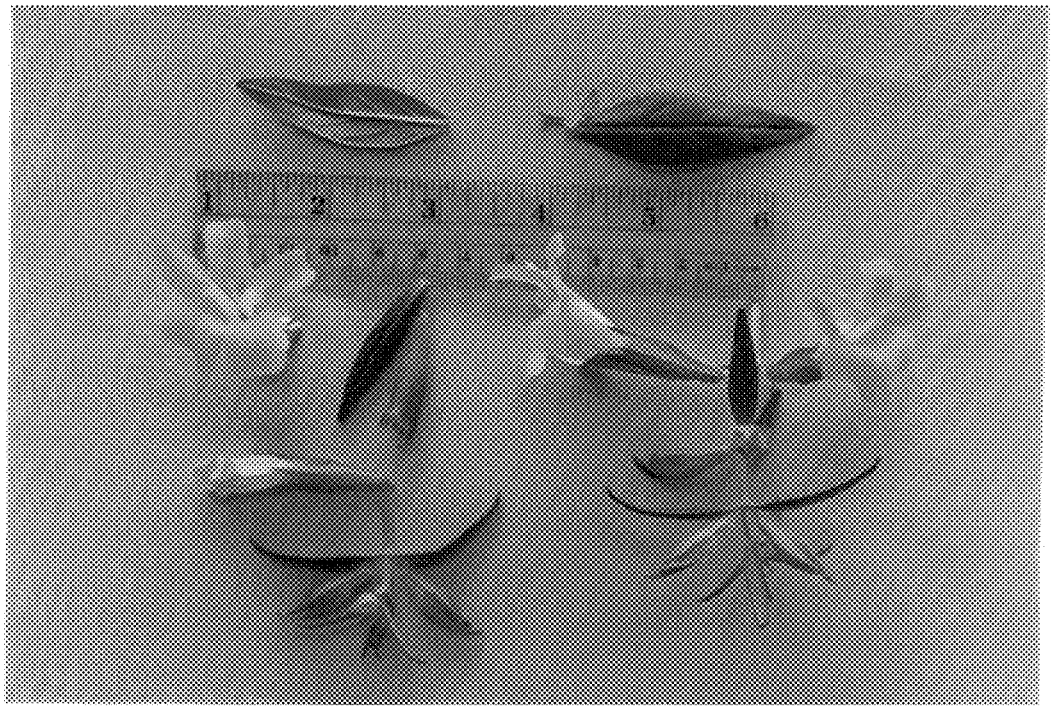

* * * * *